United States Patent
Quintana

Patent Number: 5,574,283
Date of Patent: Nov. 12, 1996

[54] NON-INVASIVE NEAR-INFRARED QUANTITATIVE MEASUREMENT INSTRUMENT

[75] Inventor: Reynaldo Quintana, Washington, D.C.

[73] Assignee: Futrex, Inc., Gaithersburg, Md.

[21] Appl. No.: 243,756

[22] Filed: May 17, 1994

Related U.S. Application Data

[63] Continuation-in-part of Ser. No. 106,758, Aug. 16, 1993, which is a continuation-in-part of Ser. No. 813,739, Dec. 30, 1991, Pat. No. 5,237,178, which is a continuation-in-part of Ser. No. 565,302, Aug. 10, 1990, Pat. No. 5,077,476, which is a continuation-in-part of Ser. No. 544,580, Jun. 27, 1990, Pat. No. 5,086,229.

[51] Int. Cl.$^6$ .................................................... G01N 33/50
[52] U.S. Cl. .................. 250/341.1; 250/339.06; 250/343
[58] Field of Search ................................ 250/341.1, 340, 250/343, 339.06, 339.07, 339.12; 128/633, 664

[56] References Cited

U.S. PATENT DOCUMENTS

| | | |
|---|---|---|
| 3,958,560 | 5/1976 | March . |
| 4,608,990 | 9/1986 | Elings . |
| 4,805,623 | 2/1989 | Jobsis . |
| 4,882,492 | 11/1989 | Schlager . |
| 4,968,137 | 11/1990 | Yount ........................................ 128/633 |
| 4,971,062 | 11/1990 | Hasebe et al. . |
| 5,007,704 | 4/1991 | McCartney .............................. 128/664 |
| 5,035,243 | 7/1991 | Muz . |
| 5,070,874 | 12/1991 | Barnes et al. . |
| 5,237,178 | 8/1993 | Rosenthal et al. .................... 250/341.1 |
| 5,311,865 | 5/1994 | Mayeux ..................................... 128/633 |
| 5,319,200 | 6/1994 | Rosenthal et al. .................... 250/341.1 |

FOREIGN PATENT DOCUMENTS

| | | |
|---|---|---|
| 74428 | 3/1983 | European Pat. Off. . |
| 140633 | 5/1985 | European Pat. Off. . |
| 262779 | 4/1988 | European Pat. Off. . |
| 426358 | 8/1991 | European Pat. Off. . |
| 3619442 | 12/1987 | Germany . |

OTHER PUBLICATIONS

Muller, "In vivo Measurement of Glucose Concentration with Lasers", *Hormone and Metabolic Research*, Supp. Series, vol. 8 (1979) Stuttgart, DE. (Best available copy).
Copy of supplementary European search report for related European patent application No. 90902878.9.

*Primary Examiner*—Davis L. Willis
*Assistant Examiner*—Richard Hanig
*Attorney, Agent, or Firm*—Rothwell, Figg, Ernst & Kurz

[57] ABSTRACT

An improved near-infrared quantitative analysis instrument includes a number of removable finger inserts each dimensioned for a different finger size, which facilitates properly aligning and fitting an individual user's finger into the optical system of the analysis instrument taking into account the size of the individual's finger. The insert according to the present invention can be also designed to accommodate samples of various substances for quantitative analyte measurement.

7 Claims, 2 Drawing Sheets

NON-INVASIVE NEAR-INFRARED QUANTITATIVE MEASUREMENT INSTRUMENT

BACKGROUND OF THE INVENTION

1. Cross-Reference to Related Applications

This application is a continuation-in-part of co-pending application Ser. No. 08/106,758, filed Aug. 16, 1993, which is a continuation-in-part of 07/813,739, filed Dec. 30, 1991, now U.S. Pat. No. 5,237,178, which is a continuation-in-part of Ser. No. 07/565,302, filed Aug. 10, 1990, now U.S. Pat. No. 5,077,476, which is a continuation-in-part of application Ser. No. 07/544,580, filed Jun. 27, 1990, now U.S. Pat. No. 5,086,229.

2. Field of the Invention

This invention relates to instruments for the non-invasive quantitative measurement of constituents in blood, such as blood glucose levels. Specifically, this invention relates to an improved analysis instrument utilizing a removable insert which facilitates positioning of an individual user's finger within the instrument according to the size of the user's finger. Additionally, the present invention is applicable to instruments for non-invasive measurement of constituents in various types of substances other than blood.

3. Description of the Background Art

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

A current type of blood glucose analytical instrumentation is available for the specific purpose of determining blood glucose levels in people with diabetes. This technology uses a small blood sample from a finger poke which is placed on a chemically treated carrier and is inserted into a portable battery operated instrument. The instrument analyzes the blood sample and provides a blood glucose level reading in a short period of time.

A different class of blood glucose analytical instruments is the near-infrared quantitative analysis instrument which noninvasively measures blood glucose, such as the type described in U.S. Pat. No. 5,077,476(Rosenthal). The non-invasive blood glucose measurement instrument analyzes near-infrared energy following interactance with venous or arterial blood, or transmission through a blood-containing body part. The instrument measures a change in light absorption that occurs, in part, due to the glucose content of the blood stream.

Non-invasive measurement instruments of this type have broad applications for the diabetic community. For example, people with diabetes have wide changes in their blood glucose content during the day which often require multiple measurements per day for good disease control. The ability to make these near-infrared blood glucose level measurements noninvasively means that more measurements will likely be made per day than would be made using the more painful blood drawing approach.

An example of a non-invasive measurement instrument is disclosed in the '229 patent wherein an individual user places the most distal portion of his or her finger within a "jaws" type arrangement. Near-infrared energy within the spectrum of interest is then impinged upon the surface of the finger and a detector is placed axially with the near-infrared beam on the opposite side of the finger to receive any near-infrared energy emerging therefrom. A microprocessor receives the amplified signal from the detector and calculates the user's blood glucose level.

Another analysis instrument is disclosed in the '476 patent which comprises a chamber formed in the instrument housing into which a user inserts his or her finger. The user's finger must be correctly placed within the chamber so that proper exposure to the near-infrared energy and detection can occur. In addition, this type of analysis instrument may measure the individual's skin temperature and use this measurement in combination with the optical measurement for calculating the blood analyte concentration. As a result, the individual's finger must properly be in contact with a skin temperature sensor to acquire the temperature measurement.

A potential limitation associated with these instruments involves obtaining inaccurate blood glucose measurements resulting from a failure to properly and securely position a user's finger, which may vary widely in size, inside the instrument. This limitation is particularly applicable to taking measurements on a child's finger. Also, proper connection with a skin temperature sensor may not occur if an individual's finger is improperly positioned within the instrument's chamber.

Thus, there is a continuing need for an improved near-infrared analysis instrument having means for for more securely positioning an individual user's finger, which vary widely in size, inside the analytical instrument.

SUMMARY OF THE INVENTION

In accordance with the present invention, a near-infrared quantitative analysis instrument for measuring a blood analyte comprises means for introducing near infrared energy into a body part of a subject, means for detecting near-infrared energy emerging from the subject and processing means for converting an electrical signal corresponding to the detected energy into a readout indicative of the blood analyte present in the blood of the subject. The analysis instrument is constructed having a housing means for housing at least the introducing means and the detecting means and a chamber means for permitting the body part to be exposed to the near-infrared energy. Also, a removable, interchangeable insert means is utilized for receiving the subject's body part and accurately placing the body part within the chamber means of the analysis instrument according to the size of the body part, such as the finger. The insert means removably engages the housing means and is aligned with the analysis instrument's optical system.

In accordance with another aspect of the invention, the removable insert means is designed to allow the noninvasive measurement of constituents in various other substances by the instrument.

DETAILED DESCRIPTION OF THE PREFERRED EMBODIMENTS

According to one embodiment of the invention, near-infrared light energy at bandwidths centering on one or more wavelengths of interest is transmitted through a blood containing portion of the body of a test subject. The near-infrared energy emerges from the test subject, generally opposite from the near-infrared source, and is detected by a detector. Following amplification of the detector generated signal, the amplified output is processed into an output signal indicating the amount of blood analyte, such as blood glucose level, in the subject's blood.

Figure 1:
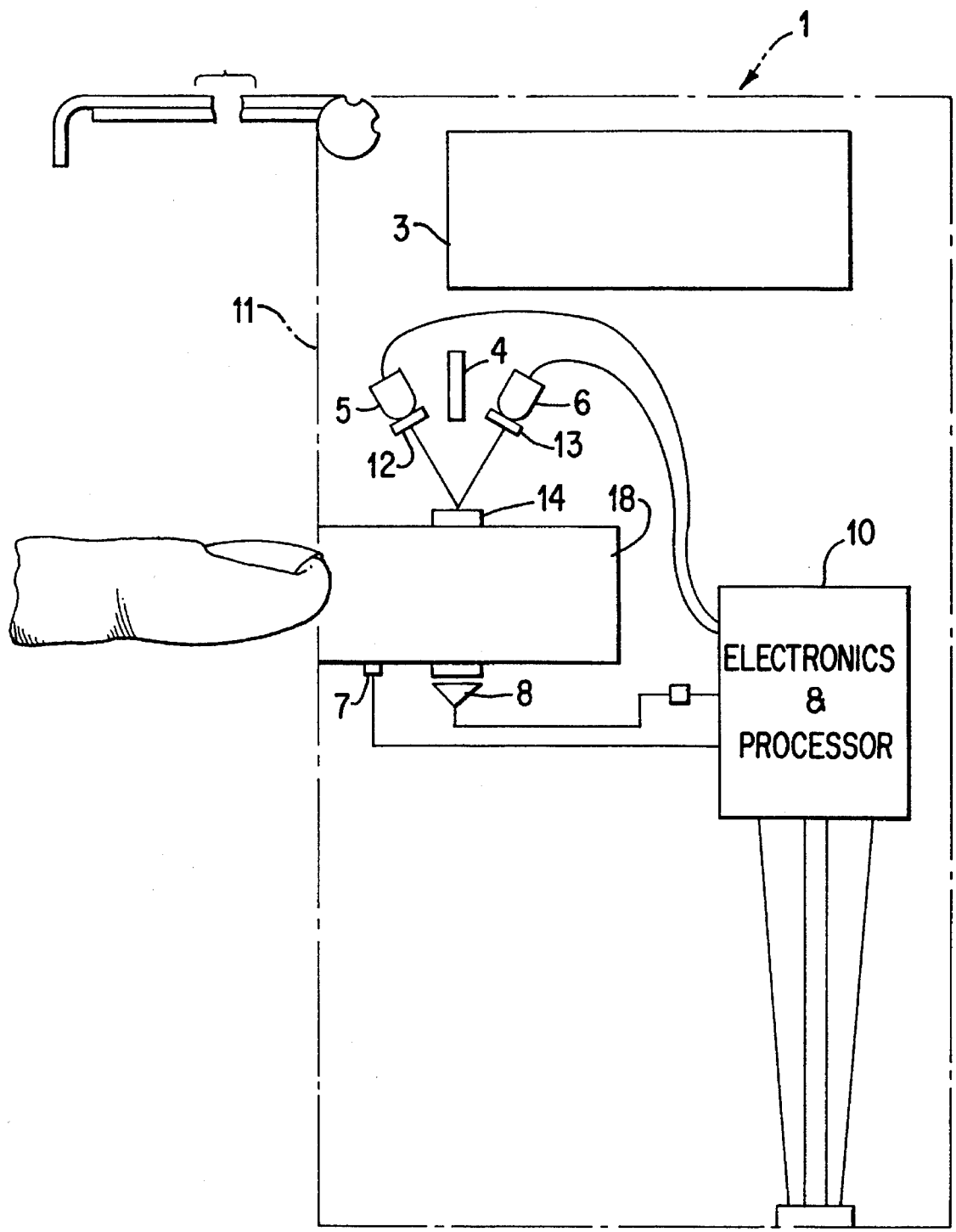
FIG. 1 illustrates a non-invasive quantitative measurement instrument according to one embodiment of the present invention.

FIG. 1 illustrates a noninvasive near-infrared quantitative analysis instrument 1 which is designed to measure a blood analyte using near-infrared transmission through a test subject's body part, such as a finger. The analytical instrument 1 contains an introducing means including at least one near-infrared energy source for introducing near-infrared energy into the test subject's finger. In one embodiment of the present invention, the introducing means comprises up to six or more near-infrared point sources (near-infrared emitting diodes or "IREDs"). IREDs 5 and 6 are shown for illustrative purposes in FIG. 1. In a preferred embodiment, the IREDs emit energy in the range of approximately 600nanometers to approximately 1100 nanometers, and preferably 1000 nanometers.

The analytical instrument also utilizes detector 8 for detecting near-infrared energy emerging from the test subject's body part. Detector 8 is electrically connected to data processing means 10 which, according to its programming, processes the signal produced by the detector 8 into a signal indicative of the quantity of blood analyte present in the test subject's blood, which is displayed on display 3. The analytical instrument 1 calculates the quantity of blood analyte present in the test subject's blood substantially as disclosed in U.S. Pat. No. 5,077,476, incorporated herein by reference.

Illustrative IREDs 5 and 6 are separated by light baffle 4 and are positioned so that the near-infrared energy is directed through window 14, which may be light scattering, and onto the test subject's skin. Window 14, however, is an optional component and is provided as a preferred embodiment. Optical filters, illustrated at 12 and 13, are positioned between each IRED and the window 14 for filtering the near-infrared light, thereby optimizing the band of near-infrared light striking the subject.

As illustrated in FIG. 1, the IREDs 5 and 6, detector 8 and processing means 10 are contained in a housing means which, preferably, is a light-weight hand-held housing unit 11. Housing means 11 further comprises a chamber means 18 for enabling the individual user's body part to be exposed to the near-infrared energy. The IREDs 5 and 6 and the detector 8 are positioned about the chamber means 18 forming an optical axis. During operation, the IREDs expose the subject's body part with near-infrared energy and detector 8 detects any energy emerging therefrom. Also, temperature sensor 7 is positioned about chamber means 18 such that it senses the user's skin temperature and produces a signal representative thereof. In one embodiment, temperature sensor 7 comes into actual contact with the user's skin. The measured skin temperature signal is input into the processing unit 10 which may be used in the calculation of the individual's blood glucose level.

However, as discussed above, potential errors in blood analyte concentration measurements may be caused by improper positioning of an individual's body part or by foreign matter degrading optical transmission.

Figure 2:
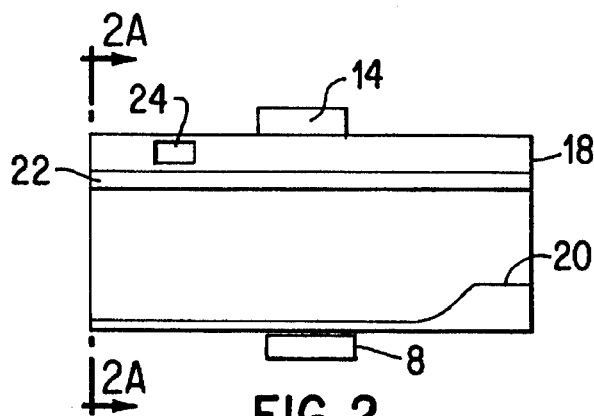
FIG. 2 is a side view of the chamber of the instrument of FIG. 1 according to the present invention.
Figure 2A:
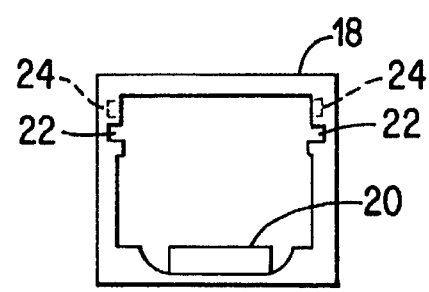
FIG. 2A is a front view of the chamber of FIG. 2 along line 2A—2A.

In accordance with the present invention, FIGS. 2 and 2A illustrate a chamber 18 of the instrument. As shown, the chamber 18 includes an elongated groove 22 at either side thereof, with a notch 24 located proximate the groove and above the groove. The bottom surface of the chamber 18 includes a finger stop 20 at the distal end of the chamber which functions to limit the distance which the finger of a subject may be inserted into the chamber.

Figure 3:
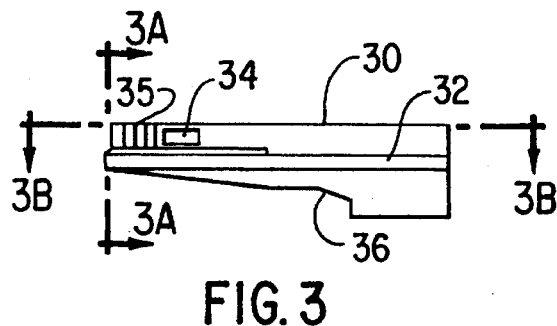
FIG. 3 is a side view of a removable insert for a large size finger according to a preferred embodiment of the present invention.
Figure 3A:
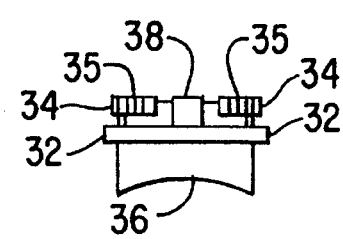
FIG. 3A is a front view of the insert of FIG. 3 along line 3A—3A.
Figure 3B:
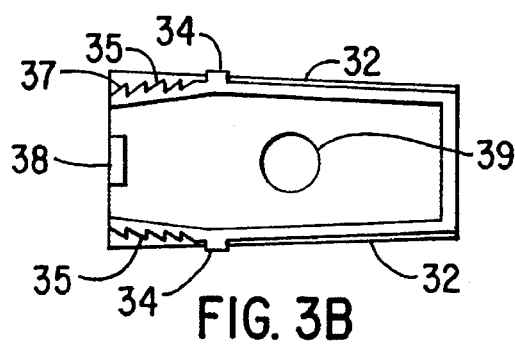
FIG. 3B is a top view of the insert of FIG. 3 along line 3B—3B.
Figure 4:
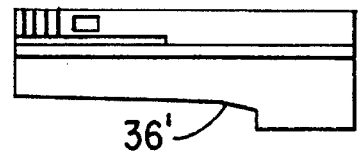
FIG. 4 is a side view of a removable insert for a medium size finger according to a preferred embodiment of the present invention.
Figure 5:
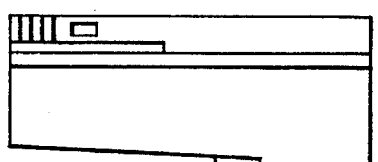
FIG. 5 is a side view of a removable insert for a small size finger according to a preferred embodiment of the present invention.

FIGS. 3, 3A and 3B illustrate a removable finger insert 30 according to a preferred embodiment of the invention. The insert 30 is preferably made of an opaque material which is also electrically conducting so as to ground any stray charge from the subject. The insert 30 includes a pair of elongated tongues 32 which are inserted into grooves 22 of the chamber 18. Tabs 34 are provided on ratchet arms 35 for engagement with notches 24 of the chamber 18. The ratchet arms 35 are constructed to have a certain degree of resiliency and are biased such that the tabs 34 will be forced into the notches 24 when the insert is fully inserted into the chamber. The ratchet arms 35 have a plurality of ratchet teeth 37 as best seen in FIG. 3B. An aperture or window 39 is provided in the top of the insert 30 at a position so as to align the aperture 39 with the window 14 to allow near-infrared energy to pass through the insert into the finger of the subject. A finger-contacting portion 36 of the insert 30 is constructed to a have a predetermined height according to the size of the particular finger of the subject using the instrument. The insert of FIG. 3 has a small height portion 36 so as to accommodate a large sized finger. FIGS. 4 and 5 illustrate inserts having medium and large height finger contacting portions 36'and 36", for accommodating medium and small sized fingers respectively.

Figure 6:
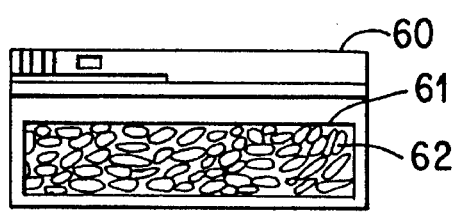
FIG. 6 is a side view of a removable insert for holding a sample of substance for quantitative analysis with a near-infrared instrument according to the present invention.

According to another aspect of the invention as shown in FIG. 6, an insert 60 is designed to hold a cuvette 61 containing samples of various substances, such as grain 62, for quantitative analyte measurement with the near-infrared instrument. Such finger inserts 60 thus allow measurements for a variety of applications, such as measurement of protein, oil and moisture content in grains and oilseeds, the properties of raw milk, the sugar content of juices, and the fat and moisture content of cheeses, among many other similar applications.

Figure 7:
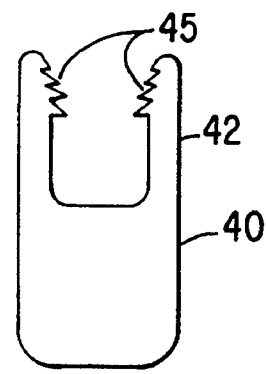
FIG. 7 is a top view of a puller tool for removing the inserts according to the present invention from the chamber of the instrument.

FIG. 7 illustrates a puller tool 40 useful in connection with the present invention for removing inserts from the chamber 18 to allow the installation of other inserts. The puller 40 includes a pair of arms 42 each having ratchet teeth 45 which are complementary to the teeth 37 of the inserts. The puller is inserted into the chamber so that the arms 42 are aligned with the ratchet arms 35 of the insert. As the arms 42 are inserted into the chamber, the ratchet arms 35 are "pinched" against stopper 38, and the teeth 45 successively engage with the teeth 37 until the puller is fully locked with the arms 35. At this point the puller tool 40 is retracted from the chamber 18, bringing with it the insert, as the teeth 45 are locked with the teeth 37. Consequently, a new insert may be installed in the chamber as desired or needed.

Although the invention has been described in connection with preferred embodiments, it is not limited to them. Modifications within the scope of the following claims will be apparent to those skilled in the art.

What is claimed is:

1. A near-infrared quantitative analysis instrument for non-invasive measurement of a blood analyte present in a body part of a subject, said analysis instrument comprising:
   (a) introducing means including a near-infrared energy source for introducing near-infrared energy into blood present in a body part of a subject;
   (b) detecting means for detecting near-infrared energy emerging from the body part;
   (c) a housing means for housing at least said introducing means and said detecting means, said housing means comprising a chamber means for enabling said body part of said subject to be exposed to said near-infrared energy, said introducing means and said detecting means being positioned about said chamber means such that near-infrared energy emitted by said introducing means is receivable by said detecting means;
   (d) a plurality of removable insert means each adapted to engage said chamber means, each of said plurality of removable insert means being dimensioned to securely and properly position within said chamber means a body part of a size different than the others of said plurality of removable insert means, wherein a specific one of said plurality of removable insert means is engaged with said chamber means according to the size of the body part of the subject under analysis; and
   (e) processing means for calculating from an electrical signal from said detection means a signal indicative of the quantity of said blood analyte present in the blood of the subject.

2. A near-infrared quantitative analysis instrument according to claim 1, wherein each of said plurality of removable insert means comprises a body part contacting portion of a predetermined thickness different from the others of said plurality of removable insert means.

3. A near-infrared quantitative analysis instrument according to claim 1, wherein said chamber means includes elongated groove means and each of said removable insert means includes elongated tongue means for engaging with said elongated groove means.

4. A near-infrared quantitative analysis instrument according to claim 3, wherein said chamber means further includes notch means proximate said elongated groove means and each of said removable insert means includes tab means for locking engagement with said notch means to lock said insert means in place within said chamber means.

5. A near-infrared quantitative analysis instrument according to claim 3, wherein each of said removable insert means includes a plurality of ratchet teeth proximate said tab means, said insert means being removable from said chamber means by puller means having a plurality of ratchet teeth complementary to said insert means ratchet teeth and interacting therewith to retract said tab means from said notch means and allow said insert means to be removed from said chamber means.

6. A method for quantitative measurement of a blood analyte present in a body part of a subject using a near-infrared quantitative analysis instrument, said instrument including a near-infrared energy source for introducing near-infrared energy into blood present in a body part of a subject, detecting means for detecting near-infrared energy emerging from the body part, housing means for housing at least said introducing means and said detecting means, said housing means comprising a chamber means for enabling said body part of said subject to be exposed to said near-infrared energy, said energy source and said detecting means being positioned about said chamber means such that near-infrared energy emitted by said introducing means is receivable by said detecting means, said method comprising the steps of:

providing a plurality of removable insert means each adapted to engage said chamber means, each of said plurality of removable insert means being dimensioned to securely and properly position within said chamber means a body part of a size different than the others of said plurality of removable insert means;

selecting a specific one of said plurality of removable insert means for engagement with said chamber means according to the size of the body part of the subject under analysis;

inserting said selected insert means into said chamber means for engagement therewith;

inserting said body part into said instrument; and actuating said instrument for calculating from an electrical signal from said detection means a signal indicative of the quantity of said blood analyte present in the blood of the subject.

7. A method for quantitative measurement of analytes present in a substance using a near-infrared quantitative analysis instrument, said instrument including a near-infrared energy source for introducing near-infrared energy into a sample of said substance, detecting means for detecting near-infrared energy emerging from the sample, housing means for housing at least said energy source and said detecting means, said housing means comprising a chamber means for enabling said sample to be exposed to said near-infrared energy, said energy source and said detecting means being positioned about said chamber means such that near-infrared energy emitted by said energy source is receivable by said detecting means, said method comprising the steps of:

providing a removable insert means adapted to engage said chamber means, said removable insert means being adapted to hold said sample of said substance, said chamber including means for removably engaging said removable insert means;

inserting said sample into said insert means;

inserting said insert means into said chamber means for engagement with said engaging means; and actuating said instrument for calculating from an electrical signal from said detection means a signal indicative of the quantity of said analyte present in said sample.

* * * * *